United States Patent
Kikuchi et al.

(10) Patent No.: US 9,463,188 B2
(45) Date of Patent: Oct. 11, 2016

(54) OSTEOPONTIN PRODUCTION INHIBITOR CONTAINING DICTYOPYRONE DERIVATIVE OR DIHYDRODICTYOPYRONE DERIVATIVE AS ACTIVE INGREDIENT

(71) Applicants: TOHOKU UNIVERSITY, Sendai-shi, Miyagi (JP); NATIONAL UNIVERSITY CORPORATION GUNMA UNIVERSITY, Maebashi-shi, Gunma (JP); FUSO PHARMACEUTICAL INDUSTRIES, LTD., Osaka-shi, Osaka (JP)

(72) Inventors: Haruhisa Kikuchi, Sendai (JP); Yoshiteru Oshima, Sendai (JP); Toshio Hattori, Sendai (JP); Yuzuru Kubohara, Maebashi (JP); Osamu Yamada, Osaka (JP); Jing Zhang, Osaka (JP); Yoshihisa Matsushita, Osaka (JP); Shinya Kida, Osaka (JP)

(73) Assignees: TOHOKU UNIVERSITY, Sendai-Shi (JP); NATIONAL UNIVERSITY CORPORATION GUNMA UNIVERSITY, Maebashi-Shi (JP); FUSO PHARMACEUTICAL INDUSTRIES, LTD., Osaka-Shi (JP)

( * ) Notice: Subject to any disclaimer, the term of this patent is extended or adjusted under 35 U.S.C. 154(b) by 0 days.

(21) Appl. No.: 14/766,543

(22) PCT Filed: Nov. 26, 2013

(86) PCT No.: PCT/JP2013/006943
§ 371 (c)(1),
(2) Date: Aug. 7, 2015

(87) PCT Pub. No.: WO2014/136161
PCT Pub. Date: Dec. 9, 2014

(65) Prior Publication Data
US 2015/0366851 A1    Dec. 24, 2015

(30) Foreign Application Priority Data
Mar. 8, 2013  (JP) .................. 2013-046197

(51) Int. Cl.
*C07D 213/02*    (2006.01)
*A61K 31/45*    (2006.01)
*A61K 31/366*    (2006.01)
*A61K 31/4412*    (2006.01)

(52) U.S. Cl.
CPC ............. *A61K 31/45* (2013.01); *A61K 31/366* (2013.01); *A61K 31/4412* (2013.01)

(58) Field of Classification Search
None
See application file for complete search history.

(56) References Cited

PUBLICATIONS

Kikuchi, "Novel Biologically Active Compounds Isolated from Unexploited Organisms, Cellular Sime Molds", Yakugaku Zasshi, 2007, vol. 127, No. 9, pp. 1431-1439, w/ English abstract, cited in ISR.
Weber, "The metastasis gene osteopontin: a candidate target for cancer therapy", Biochim Biophys Acta, 2001, vol. 1552, pp. 61-85, cited in specification and ISR.
Kikuchi, et al., "Structural requirements of dictyopyrones isolated from *Dictyostelium* spp. in the regulation of Dictyostelium development and in anti-leukemic activity", Bioorganic & Medicinal Chemistry, vol. 12, pp. 3203-3214, 2004, cited in specification and ISR.
Kikuchi, et al., "Dihydrodictyopyrone A and C: new members of dictyopyrone family isolated from Dictyostelium cellular slime molds", Tetrahedron Letters, 2007, vol. 48, pp. 5905-5909, cited in specification and ISR.
Miyauchi, et al., "Recognition of Osteopontin and Related Peptides by an alpha v beta 3 Integrin Stimulates Immediate Cell Signals in Osteoclasts", The Journal of Biological Chemistry, Oct. 25, 1991, vol. 266, No. 30, pp. 20369-20374, cited in specification.
Senger, et al., "Secreted Phosphoproteins Associated with Neoplastic Transformation: Close Homology with Plasma Proteins Cleaved during Blood Coagulation" Cancer Research, 1988, vol. 48, pp. 5770-5774, cited in specification.
Brown, et al., "Osteopontin Expression in Human Carcinomas", American Journal of Pathology, Sep. 1994, vol. 145, No. 3, pp. 610-623, cited in specification.
Saitoh, et al, "Expression of Osteopontin in Human Glioma Its Correlation with the Malignancy", Laboratory Investigation, 1995, vol. 72, No. 1, pp. 55-63, cited in specification.
Suzuki, et al., "Osteopontin Gene Expression Determines Spontaneous Metastatic Performance of Orthotopic Human Breast Cancer Xenografts", The American Journal of Pathology, Aug. 2007, vol. 171, No. 2, pp. 682-692, cited in specification.
Matsuura, et al., "Statin-mediated reduction of osteopontin expression induces apoptosis and cell growth arrest in ovarian clear cell carcinoma", Oncology Reports, 2011, vol. 25, pp. 41-47, cited in specification.
International Search Report dated Mar. 4, 2014, issued in counterpart application No. PCT/JP2013/006943 (2 pages).

*Primary Examiner* — Zinna Northington Davis
(74) *Attorney, Agent, or Firm* — Westerman, Hattori, Daniels & Adrian, LLP

(57) ABSTRACT

Disclosed herein is an osteopontin production inhibitor capable of preventing a disease resulting from increased production of osteopontin. The osteopontin production inhibitor contains a dictyopyrone derivative or a dihydrodictyopyrone derivative as an active ingredient. The dictyopyrone derivative is preferably a compound represented by Chemical Formula 1 or 2, and the dihydrodictyopyrone derivative is preferably a compound represented by Chemical Formula 3 or 4.

6 Claims, 3 Drawing Sheets

Each value was expressed as mean (n=2)

OSTEOPONTIN PRODUCTION INHIBITOR CONTAINING DICTYOPYRONE DERIVATIVE OR DIHYDRODICTYOPYRONE DERIVATIVE AS ACTIVE INGREDIENT

TECHNICAL FIELD

The present invention relates to an osteopontin (OPN) production inhibitor containing a dictyopyrone derivative or a dihydrodictyopyrone derivative as an active ingredient and capable of preventing or improving a disease (e.g., cancer metastasis) caused by increased production of OPN.

BACKGROUND ART

OPN is a secreted acidic phosphorylated glycoprotein with a molecular weight of about 41 kDa identified as a major non-collagenous protein constituting the matrix of bone tissue where calcium is deposited. OPN is widely expressed in milk, urine, renal tubular, osteoclasts, osteoblasts, macrophages, activated T cells, and various tumor tissues. OPN has been considered to play a role in anchoring osteoclasts to hydroxyapatite in bone matrix (Nonpatent Literature 1), but other various functions of OPN have been reported such as involvement in cell adhesion, cell migration, control of nitric monoxide production, tumors, and the immune system.

The expression of OPN correlates with tumor progression and has an association with cancer metastasis. OPN has been detected in plasma of patients with lung cancer, liver cancer, breast cancer, or prostate cancer (Nonpatent Literature 2). It has been reported that the expression of OPN mRNA in a cancer site is higher than that in a normal site (Nonpatent Literature 3), and it has also been reported that the expression of OPN in glioma tends to correlate with the degree of malignancy (Nonpatent Literature 4). The correlation between OPN expression and tumor has been confirmed also in animal models (Nonpatent Literature 5). Based on these recent findings about OPN, suppression of production of OPN that promotes metastasis and invasion of tumor cells has come to be considered as one of new approaches of an anti-cancer drug that prevents cancer metastasis (Nonpatent Literature 6).

CITATION LIST

Nonpatent Literature

NPL 1: Miyauchi A, Alvarez J, Greenfield E M, Teti A, Grano M, Colucci S, Zambonin-Zallone A, Ross F P, Teitelbaum S L, Cheresh D, Hruska K A. (1991) Recognition of osteopontin and related peptides by an alpha v beta 3 integrin stimulates immediate cell signals in osteoclasts. *J Biol Chem* 266, 20369-20374

NPL 2: Senger D R, Perruzzi C A, Gracey C F, Papadopoulos A, Tenen D G. (1988) Secreted phosphoproteins associated with neoplastic transformation: close homology with plasma proteins cleaved during blood coagulation. *Cancer Res* 48, 5770-5774

NPL 3: Brown L F, Papadopoµlos-Seigiou A, Brygida B, Manseau E J, TognazziK, Perruzzi C A, Dvorak H F, Senger D R. (1994) Osteopontin expression in human carcinoma. *Am J Pathol.* 145, 610-623

NPL 4: Saitoh Y, Kuratsu J I, Takeshima H, Yamamoto S, Ushio Y (1995) Expression of osteopontin in human glioma. *Lab Invest* 72, 55-63.

NPL 5: Suzuk M, Mose E, Galloy C, and Tarin T (2007) Osteopontin Gene Expression Determines Spontaneous Metastatic Performance of Orthotopic Human Breast Cancer Xenografts. *Am J Pathol* 171, 682-692

NPL 6: Weber G F (2001) Review: The metastasis gene osteopontin: a candidate target for cancer therapy. *Biochim Biophys Acta* 1552, 61-85

NPL 7: Kikuchi H, Sasaki K, Sekiya J, Maeda M, Amagai A, Kubohara Y and Oshima Y (2004) Dihydrodictyopyrone A and C: new members of dictyopyrone family isolated from Dictyostelium cellular slime molds *Bioorg Med Chem* 12, 3203-3214

NPL 8: Matsuura M, Suzuki T, Suzuki M, Tanaka R, Ito E and Saito T (2011) Statin-mediated reduction of osteopontin expression induces apoptosis and cell growth arrest in ovarian clear cell carcinoma. *Oncol Rep* 25, 41-47

NPL 9: Haruhisa Kikuchi, Koji Nakamura, Yuzuru Kubohara, Naomi Gokan, Kohei Hosaka, Yasuo Maedad and Yoshiteru Oshima, *Tetrahedron Letters* 48 (2007) 5905-5909

SUMMARY OF INVENTION

Technical Problem

As described above, suppression of OPN production has the potential to prevent cancer metastasis. As drugs having OPN production inhibitory effect, insulin resistance improvers as PPAR-γ (Peroxysome Proliferator-Activated Receptor-γ) agonists (troglitazone, pioglitazone, rosiglitazone), non-steroid anti-inflammatory drugs (e.g., indomethacin, ibuprofen), statin-based drugs for treatment of hypercholesteremia as HMG-CoA reductase inhibitors (e.g., rosuvastatin, rovastatin, simvastatin, pravastatin, fluvastatin, atorvastatin, cerivastatin, pitavastatin, mevastatin) are known.

Meanwhile, cellular slime molds are protists widely distributed in the soil surface layer. Cellular slime molds have both animal-like and plant-like properties very different from each other and show both unicellular and multicellular forms, and their life cycle includes major processes of developmental systems of multicellular organisms, such as cell movement, cytokinesis, and differentiation. Such cellular slime molds are greatly different from organism species conventionally and commonly used in natural product chemistry, and are therefore expected to produce various novel compounds.

It is therefore an object of the present invention to provide an OPN production inhibitor capable of preventing a disease (e.g., cancer metastasis) resulting from increased production of OPN.

Solution to Problem

In order to find a compound that suppresses OPN gene expression, the present inventors have performed screening for secondary metabolites of cellular slime molds such as *D. discoideum* with the use of cell strains that express luciferase as a reporter gene under control of OPN promoter.

As a result, the present inventors have found compounds that suppress luciferase expression from among dictyopyrone derivatives and dihydrodictyopyrone derivatives.

Further, the present inventors have also found that such compounds that suppress luciferase activity under control of OPN promoter reduce the amount of OPN produced by a human non-small cell lung cancer-derived cell line A549 or a human liver cancer-derived cell line HepG2. Further, the present inventors have also found that in Wound-Healing assay, the dictyopyrone derivatives and dihydrodictyopyrone derivatives suppress the ability of OPN to migrate cells, which is the physiological function of OPN, and that in matrix gel invasion assay, the dictyopyrone derivatives and dihydrodictyopyrone derivatives suppress the metastatic and invasive capacity of cells. These findings have led to the completion of the present invention.

Specifically, the present invention relates to an osteopontin production inhibitor containing a dictyopyrone derivative or a dihydrodictyopyrone derivative as an active ingredient.

It has been reported that some dictyopyrone derivatives and dihydrodictyopyrone derivatives have the activity of suppressing the growth of human leukemia cell-derived K562 cells (Nonpatent Literature 7), but their OPN production inhibitory effect has not heretofore been reported.

The dictyopyrone derivative is preferably a compound represented by the following chemical formula 1 or 2.

[Chemical Formula 1]

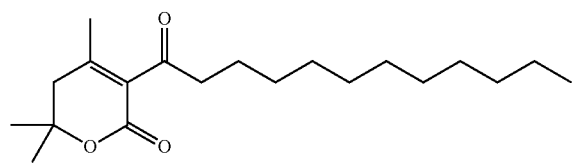

[Chemical Formula 2]

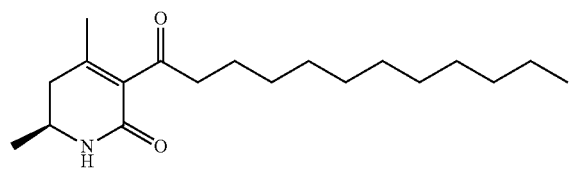

The dihydrodictyopyrone derivative is preferably a compound represented by the following chemical formula 3 or 4.

[Chemical Formula 3]

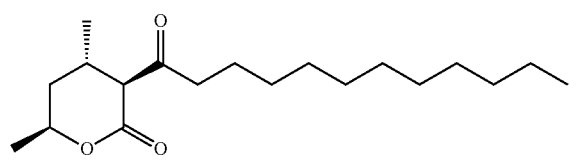

[Chemical Formula 4]

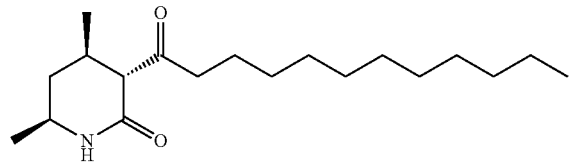

[Chemical Formula 4]

Advantageous Effects of Invention

The OPN production inhibitor according to the present invention containing a dictyopyrone derivative or a dihydrodictyopyrone derivative as an active ingredient is an OPN production inhibitor whose mechanism of action is different from that of an insulin resistance improver or a statin-based drug for treatment of hypercholesteremia.

DESCRIPTION OF EMBODIMENTS

Figure 1:
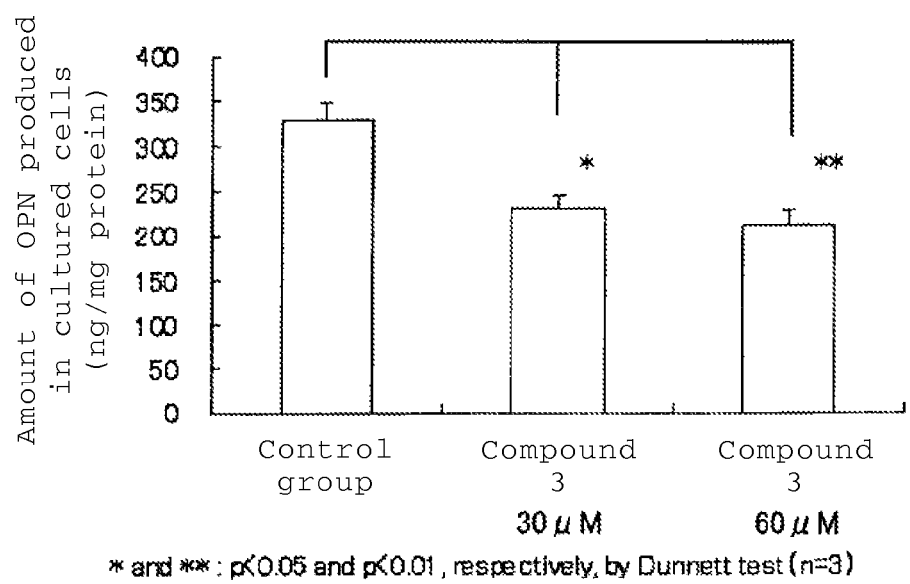
FIG. 1 is a graph showing the effect of addition of a compound 3 (compound represented by the chemical formula 3) on suppressing OPN production by A549 cells.

An embodiment of the present invention will be described with reference to the accompanying drawings as appropriate. The present invention is not limited to the following description.

<A. Method for Confirming Luciferase Expression Inhibitory Effect Under Control of OPN Promoter>

A reporter vector pOPN1-luc obtained by inserting a human OPN promoter sequence (−765 to 23) into the multiple cloning site of pGL-3 basic vector (Promega) expresses luciferase when transfected into animal cells. This pOPN1-luc was transfected into a human non-small cell lung cancer-derived cell line A549 together with pPUR (Clontech) that expresses a puromycin resistance gene (puromycin-N-acetyl-transferase gene), and cells that could grow in a puromycin-supplemented medium and expressed luciferase were selected. The selected cells were named A549/OPNluc cells and used for observation of luciferase expression inhibitory effect under control of OPN promoter, as described later.

A test compound was added to a culture liquid containing A549/OPNluc cells to observe its influence on the amount of luciferase expressed in the cells. Here, it can be considered that when the test compound has cytotoxity or cell growth-suppressing effect, the total expression level of luciferase is reduced due to a reduction in the number of living cells that depends on the concentration of the test compound, and therefore the luciferase expression inhibitory effect of the test compound under control of OPN promoter cannot be properly evaluated. For this reason, WST assay for quantification of cell proliferation ability or cell viability by colorimetric measurement was first performed to determine IC50 (concentration for 50% inhibition of cell growth) of the test compound for cell growth. Then, luciferase activity measurement was performed to determine EC50 (concentration for 50% inhibition of luciferase expression) of the test compound for luciferase expression under control of OPN promoter.

A1) WST Assay

A549/OPNluc cells were suspended in DMEM medium containing 10% fetal calf serum (FCS) and 1% penicillin/streptomycin (P/S) at $3 \times 10^4$ cells/mL to obtain a cell suspension, and 100 µL of the cell suspension was dispensed into each well of a 96-well plate. In order to perform the assay in triplicate, 3 wells were prepared for a control group and 3 wells were prepared for each test compound-treated group at each concentration. After the dispensing, the 96-well plate was incubated in a $CO_2$ incubator (at 37° C. and 5% $CO_2$) for 24±4 hours.

The test compound was dissolved in dimethylsulfoxide (DMSO) to obtain a 50 mmol/L solution, and the test compound solution was stored at −80° C. The test compound solution was diluted with DMSO in 2-fold dilution series (usually, in the range of 0.31 mmol/L to 20 mmol/L) to prepare test compound solutions whose concentration varied by two fold for WST assay.

Only DMSO (control) or the diluted test compound (sample) solution was dispensed in an amount of 0.5 μL into each well containing the cell suspension (200-fold dilution). The solution in each well was mixed with a vortex mixer, and then the 96-well plate was incubated in a $CO_2$ incubator (at 37° C. and 5% $CO_2$) for 48±4 hours. Then, 10 μL of Premix WST-1 Reagent (TAKARA BIO INC.) was added to each well. The solution in each well was mixed with a vortex mixer, and then the 96-well plate was incubated at 37° C. and 5% $CO_2$. After 60 minutes or 120 minutes, absorbance values (450 nm) were measured using a microplate reader (Bio-Rad; Benchmark or Thermo Scientific; Varioskan Flash).

The absorbance values of the control wells and the absorbance values of the sample wells at each concentration were input into an Excel file to determine the percentages of absorbance values of the sample wells at each concentration with respect to the average of absorbance values of the control wells. From the determined values, a fitted curve was determined by the method of least squares to calculate IC50.

A2) Luciferase Assay

The same steps as in the above-described WST assay were performed in which only DMSO (control) or the diluted test compound (sample) solution was added in an amount of 0.5 μL to each well containing the cell suspension to achieve 200-fold dilution, and the solution in each well was mixed with a vortex mixer, and the 96-well plate was incubated in a $CO_2$ incubator (at 37° C. and 5% $CO_2$) for 48±4 hours.

A luciferase reagent was prepared by dissolving Luciferase Assay Substrate (hereinafter, referred to as "LAS") supplied in Luciferase Assay Systems (Promega: Cat# E1500) with Luciferase Assay Buffer (LAB). 5× Cell Culture Lysis Reagent (hereinafter, referred to as "CCLR") was diluted with water 5-fold to prepare 1×CCLR.

After the incubation for 48±4 hours, the medium in each well was completely removed, and 50 μL of 1×CCLR was dispensed into each well. The 96-well plate was allowed to stand at room temperature for 30 minutes, and then 1×CCLR in each well was used as an assay sample. The luciferase reagent of 100 μL was placed in a tube for chemiluminescence measurement, and 20 μL of the assay sample was added to the tube and mixed with the luciferase reagent to measure chemiluminescence (Relative Luminescence Intensity: RLU) using Tuner Design Luminometer 20/20 (Promega).

The RLU values of the control wells and the RLU values of the sample wells at each concentration were input into an Excel file, and the percentages of RLU values of the sample wells at each concentration with respect to the average of RLU values of the control wells were determined. From these values, a fitted curve was determined by the method of least squares to calculate EC50.

Table 1 shows IC50 values calculated by WST assay and EC50 values calculated by luciferase assay of dictyopyrone derivatives and dihydrodictyopyrone derivatives as test compounds represented by the following chemical formulas 1 to 16.

[Chemical Formula 5]

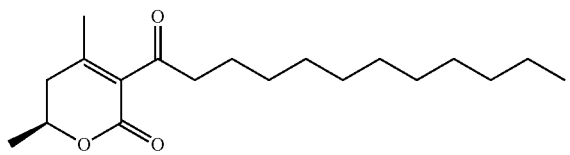

[Chemical Formula 6]

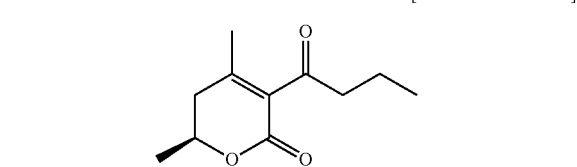

[Chemical Formula 7]

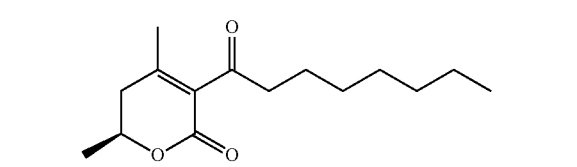

[Chemical Formula 8]

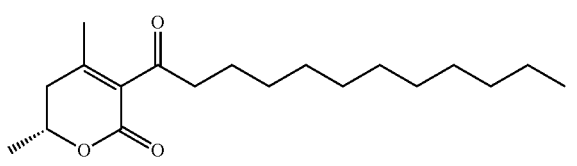

[Chemical Formula 9]

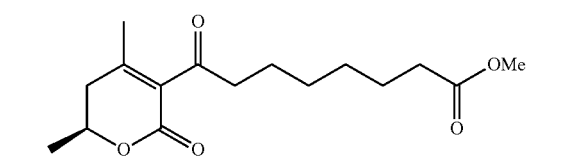

[Chemical Formula 10]

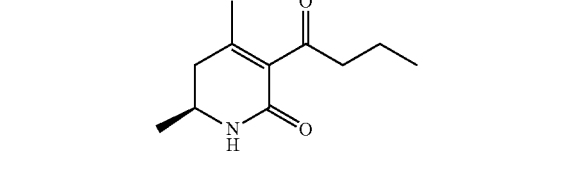

[Chemical Formula 11]

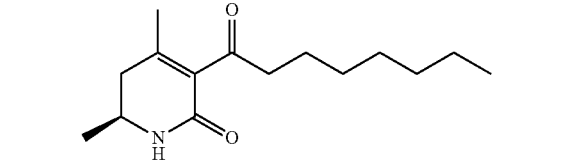

[Chemical Formula 12]

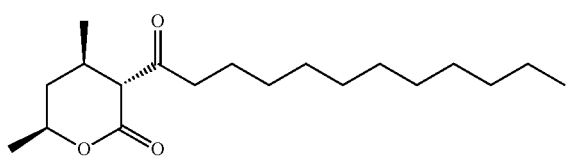

-continued

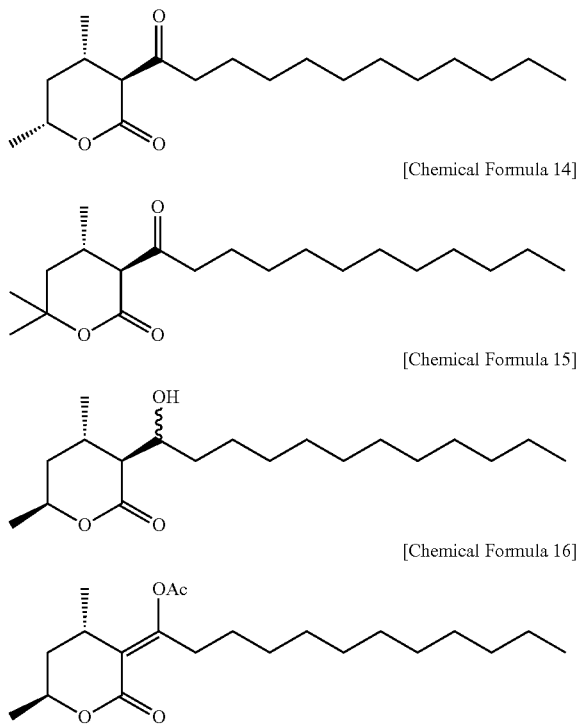

[Chemical Formula 13]

[Chemical Formula 14]

[Chemical Formula 15]

[Chemical Formula 16]

Here, the compounds represented by the chemical formulas 1, 2, 5 to 8 were produced according to a production method disclosed in Nonpatent Literature 7, and the compounds represented by the chemical formulas 3, 12, 13, 15, and 16 were produced according to a production method disclosed in Nonpatent Literature 9.

<Method for Producing Compound Represented by Chemical Formula 4>

(S)-3-dodecanoyl-5,6-dihydro-4,6-dimethyl-1H-pyridin-2-one of 5 mg synthesized as described in Nonpatent Literature 7 was dissolved in 1 mL of methanol. Palladium-carbon (Pd 5%) of 1 mg was added, and the mixture was stirred at room temperature for 2 hours in an atmosphere of hydrogen to obtain a reaction liquid. The reaction liquid was filtered to remove palladium-carbon, and the filtrate was subjected to distillation under a reduced pressure. The residue was subjected to silica gel column chromatography, and 4 mg of the compound represented by the chemical formula 4 was obtained from fractions eluted with hexane-ethyl acetate (4:1).

The obtained compound was analyzed by electron impact mass spectrometry (EIMS) and NMR. The results of EIMS and NMR are as follows.

$^1$H-NMR (400 MHz, CDCl$_3$) d 5.76 (1H, br. s), 3.52-3.64 (1H, m), 3.05 (1H, d, J=11.2 Hz), 2.81 (1H, dt, J=17.8, 7.5 Hz), 2.52 (1H, dt, J=17.8, 7.4 Hz), 2.28-2.41 (1H, m), 1.87 (1H, dt, J=13.0, 2.3 Hz), 1.52-1.68 (3H, m), 1.23-1.36 (16H, s), 1.17 (3H, d, J=6.4 Hz), 0.94 (3H, d, J=6.5 Hz), 0.88 (3H, t, J=6.4 Hz).

EIMS m/z (rel. int) 309 [M]$^+$ (11), 294 (5), 182 (10), 169 (13), 127 (100), 112 (55).

<Method for Producing Compound Represented by Chemical Formula 9>

Suberic acid monomethyl ester of 297 mg was dissolved in 8 mL of methylene chloride, and 250 mg of Meldrum's acid, 453 mg of 1-ethyl-3-(3-dimethylaminopropyl)carbodiimide hydrochloride, and 19 mg of 4-(dimethylamino)pyridine were added, and the mixture was stirred at room temperature for 4 hours to obtain a reaction liquid. Thirty milliliters of 0.5 M hydrochloric acid was added to the reaction liquid, and the mixture was subjected to extraction with 30 mL of ethyl acetate three times. After the extraction, all the ethyl acetate layers were combined, washed with 60 mL of water and then with 60 mL of saturated salt water, and dried with anhydrous sodium sulfate, and then the solvent was removed by distillation under a reduced pressure. The residue was dissolved in 5 mL of toluene, and 246 mg of (2S,4S)-2,4-pentanediol was added, and the mixture was stirred at 120 C. for 2 hours to obtain a reaction liquid. After returned to room temperature, the reaction liquid was subjected to distillation under a reduced pressure. The residue was subjected to silica gel column chromatography, and 200 mg of 1-(1S,3S)-3-hydroxy-1-methylbutyl 10-methyl 3-oxodecanedioate was obtained from fractions eluted with hexane-ethyl acetate (3:1).

1-(1S,3S)-3-hydroxy-1-methylbutyl 10-methyl 3-oxodecanedioate of 196 mg was dissolved in 8 mL of methylene chloride, and 109 mg of N-methylmorpholine N-oxide, 311 mg of powdered molecular sieves 4A, and 11 mg of tetrapropylammonium perruthenate were added in order, and the mixture was stirred at room temperature for 5 hours to obtain a reaction liquid. The reaction liquid was filtered, and the filtrate was subjected to distillation under a reduced pressure. The residue was subjected to silica gel column chromatography, and 133 mg of 1-(S)-1-methyl-3-oxobutyl 10-methyl 3-oxodecanedioate was obtained from fractions eluted with hexane-ethyl acetate (4:1).

1-(S)-1-methyl-3-oxobutyl 10-methyl 3-oxodecanedioate of 126 mg was dissolved in 2 mL of ethanol, and 41 mg of sodium ethoxide was added, and the mixture was stirred at room temperature for 10 hours to obtain a reaction liquid. The reaction liquid was poured into 20 mL of 0.5 M hydrochloric acid, and the mixture was subjected to extraction with 20 mL of ethyl acetate three times. After the extraction, all the ethyl acetate layers were combined, washed with 40 mL of water and then with 40 mL of saturated salt water, and dried with anhydrous sodium sulfate, and then the solvent was removed by distillation under a reduced pressure. The residue was subjected to silica gel column chromatography, and 88 mg of methyl (S)-8-(4,6-dimethyl-2-oxo-5,6-dihydro-2H-pyran-3-yl)-8-Oxooctanoate (compound represented by chemical formula 9) was obtained from fractions eluted with hexane-ethyl acetate (4:1).

The obtained compound was analyzed by electron impact mass spectrometry (EIMS) and NMR. The results of EIMS and NMR are as follows.

$^1$H-NMR (400 MHz, CDCl$_3$) d 4.50-4.60 (1H, m), 3.67 (3H, s), 2.74 (1H, dt, J=17.3, 7.4 Hz), 2.73 (1H, dt, J=17.3, 7.4 Hz), 2.45 (1H, ddq, J=17.9, 11.6, 0.9 Hz), 2.31 (1H, dd, J=17.9, 3.8 Hz), 2.30 (2H, t, J=7.4 Hz), 2.01 (3H, d, J=0.9 Hz), 1.58-1.68 (4H, m), 1.44 (3H, d, J=6.4 Hz), 1.30-1.38 (4H, m).

EIMS m/z (rel. int) 296 [M]$^+$ (6), 281 (10), 265 (11), 246 (14), 181 (20), 168 (83), 153 (100), 109 (30).

<Method for Producing Compound Represented by Chemical Formula 10>

(S)-2-[1-Methyl-2-(2-methyl-1,3-dioxan-2-yl)ethyl]-isoindole-1,3-dione of 300 mg synthesized as described in Nonpatent Literature 7 was dissolved in 6 mL of methanol, and 1038 mg of hydrazine monohydrate was added, and the mixture was heated to reflux for 6 hours to obtain a reaction liquid. After returned to room temperature, the reaction liquid was mixed with 30 mL of a 1 M aqueous sodium hydroxide solution, and the mixture was subjected to extraction with 30 mL of ethyl acetate three times. After the extraction, all the ethyl acetate layers were combined, washed with 60 mL of water and then with 60 mL of saturated salt water, and dried with anhydrous sodium sulfate, and then the solvent was removed by distillation under a reduced pressure. The residue was dissolved in 6 mL of toluene, and 565 mg of 5-butanoyl-2,2-dimethyl-1,3-dioxane-4,6-dione was added, and the mixture was heated to reflux for 15 hours to obtain a reaction liquid. After returned to room temperature, the reaction liquid was subjected to distillation under a reduced pressure. The residue was subjected to silica gel column chromatography, and 140 mg of (S)—N-[1-methyl-2-(2-methyl-1,3-dioxan-2-yl)ethyl]-3-oxohexanamide was obtained from fractions eluted with hexane-ethyl acetate (2:1).

(S)—N-[1-methyl-2-(2-methyl-1,3-dioxan-2-yl)ethyl]-3-oxohexanamide of 115 mg was dissolved in 4 mL of an 80% aqueous acetic acid solution, and the mixture was stirred at room temperature for 7 hours to obtain a reaction liquid. The reaction liquid was subjected to distillation under a reduced pressure, and the residue was subjected to silica gel column chromatography, and 59 mg of (S)—N-(1-methyl-3-oxobutyl)-3-oxodecanamide was obtained from fractions eluted with hexane-ethyl acetate (2:1).

(S)—N-(1-methyl-3-oxobutyl)-3-oxodecanamide of 11 mg was dissolved in 1 mL of ethanol, and 5 mg of sodium ethoxide was added, and the mixture was stirred at room temperature for 8 hours to obtain a reaction liquid. The reaction liquid was poured into 10 mL of 0.5 M hydrochloric acid, and the mixture was subjected to extraction with 10 mL of ethyl acetate three times. After the extraction, all the ethyl acetate layers were combined, washed with 20 mL of water and then with 20 mL of saturated salt water, and dried with anhydrous sodium sulfate, and then the solvent was removed by distillation under a reduced pressure. The residue was subjected to silica gel column chromatography, and 4 mg of (S)-3-butanoyl-5,6-dihydro-4,6-dimethyl-1H-pyridin-2-one (compound represented by chemical formula 10) was obtained from fractions eluted with hexane-ethyl acetate (2:1).

The product was analyzed by electron impact mass spectrometry (EIMS) and NMR. The results of EIMS and NMR are as follows.

$^1$H-NMR (400 MHz, CDCl$_3$) d 5.45 (1H, br. s), 3.66-3.78 (1H, m), 2.71 (2H, t, J=7.4 Hz), 2.31 (1H, dd, J=17.6, 7.6 Hz), 2.23 (1H, dd, J=17.6, 7.2 Hz), 1.93 (3H, s), 1.64 (2H, quint, J=7.4 Hz), 1.24, (3H, d, J=6.4 Hz), 0.94 (3H, t, J=7.4 Hz).

EIMS m/z (rel. int) 195 [M]$^+$ (19), 180 (100), 152 (54), 109 (22).

<Method for Producing Compound Represented by Chemical Formula 11>

(S)-2-[1-Methyl-2-(2-methyl-1,3-dioxan-2-yl)ethyl]-isoindole-1,3-dione of 300 mg synthesized as described in Nonpatent Literature 7 was dissolved in 6 mL of methanol, and 1038 mg of hydrazine monohydrate was added, and the mixture was heated to reflux for 6 hours to obtain a reaction liquid. After returned to room temperature, the reaction liquid was mixed with 30 mL of a 1 M aqueous sodium hydroxide solution, and the mixture was subjected to extraction with 30 mL of ethyl acetate three times. After the extraction, all the ethyl acetate layers were combined, washed with 60 mL of water and then with 60 mL of saturated salt water, and dried with anhydrous sodium sulfate, and then the solvent was removed by distillation under a reduced pressure. The residue was dissolved in 6 mL of toluene, and 564 mg of 2,2-dimethyl-5-octanoyl-1,3-dioxane-4,6-dione was added, and the mixture was heated to reflux for 15 hours to obtain a reaction liquid. After returned to room temperature, the reaction liquid was subjected to distillation under a reduced pressure. The residue was subjected to silica gel column chromatography, and 51 mg of (S)—N-[1-methyl-2-(2-methyl-1,3-dioxan-2-yl)ethyl]-3-oxodecanamide was obtained from fractions eluted with hexane-ethyl acetate (2:1).

(S)—N-[1-methyl-2-(2-methyl-1,3-dioxan-2-yl)ethyl]-3-oxodecanamide of 47 mg was dissolved in 3 mL of an 80% aqueous acetic acid solution, and the mixture was stirred at room temperature for 7 hours to obtain a reaction liquid. The reaction liquid was subjected to distillation under a reduced pressure, and the residue was subjected to silica gel column chromatography, and 38 mg of (S)—N-(1-methyl-3-oxobutyl)-3-oxodecanamide was obtained from fractions eluted with hexane-ethyl acetate (2:1).

(S)—N-(1-methyl-3-oxobutyl)-3-oxodecanamide of 23 mg was dissolved in 2 mL of N,N-dimethylformamide, and 3 mg of sodium hydride (60%, dispersed in mineral oil) was added, and the mixture was stirred at room temperature for 10 hours to obtain a reaction liquid. The reaction liquid was poured into 10 mL of 0.5 M hydrochloric acid, and the mixture was subjected to extraction with 10 mL of ethyl acetate three times. After the extraction, all the ethyl acetate layers were combined, washed with 20 mL of water and then with 20 mL of saturated salt water, and dried with anhydrous sodium sulfate, and then the solvent was removed by distillation under a reduced pressure. The residue was subjected to silica gel column chromatography, and 9 mg of (S)-5,6-dihydro-4,6-dimethyl-3-octanoyl-1H-pyridin-2-one (compound represented by the chemical formula 11) was obtained from fractions eluted with hexane-ethyl acetate (2:1).

The product was analyzed by electron impact mass spectrometry (EIMS) and NMR. The results of EIMS and NMR are as follows.

$^1$H-NMR (400 MHz, CDCl$_3$) d 5.52 (1H, br. s), 3.65-3.78 (1H, m), 2.72 (2H, t, J=7.6 Hz), 2.31 (1H, dd, J=17.2, 5.6 Hz), 2.23 (1H, dd, J=17.2, 7.2 Hz), 1.92 (3H, s), 1.60 (2H, quint, J=7.6 Hz), 1.23-1.35 (8H, m), 1.24 (3H, d, J=6.8 Hz), 0.87 (3H, t, J=7.0 Hz).

EIMS m/z (rel. int) 251 [M]$^+$ (33), 236 (57), 180 (100), 167 (69), 152 (76), 109 (23).

<Method for Producing Compound Represented by Chemical Formula 14>

3-dodecanoyl-5,6-dihydro-4,6,6-trimethyl-2H-pyran-2-one of 10 mg synthesized as described in Nonpatent Literature 7 was dissolved in 1 mL of ethyl acetate. One milligram of 20% palladium hydroxide-carbon was added, and the mixture was stirred at room temperature for 20 hours in an atmosphere of hydrogen to obtain a reaction liquid. The reaction liquid was filtered to remove palladium-carbon, and the filtrate was subjected to distillation under a reduced pressure. The residue was subjected to silica gel column chromatography, and 9 mg of the compound represented by the chemical formula 14 was obtained from fractions eluted with hexane-ethyl acetate (19:1).

The product was analyzed by electron impact mass spectrometry (EIMS) and NMR. The results of EIMS and NMR are as follows.

$^1$H-NMR (400 MHz, CDCl$_3$) d 3.13 (1H, d, J=10.8 Hz), 2.87 (1H, dt, J=14.8, 7.2 Hz), 2.59-2.67 (1H, m), 2.55 (1H, dt, J=14.8, 6.8 Hz), 1.84 (1H, dd, J=13.4, 4.0 Hz), 1.57-1.66

(2H, m), 1.51 (1H, t, J=13.4 Hz), 1.43 (3H, s), 1.42 (3H, s), 1.25-1.31 (16H, m), 0.95 (3H, d, J=6.4 Hz), 0.88 (3H, t, J=6.6 Hz).

EIMS m/z (rel. int) 324 [M]$^+$ (3), 309 (6), 84 (100).

TABLE 1

|  | IC50 (µM) | EC50 (µM) |
|---|---|---|
| Dictyopyrone derivatives | | |
| Chemical formula 1 | 128.9 | 24.4 |
| Chemical formula 2 | 59.1 | 29.5 |
| Chemical formula 5 | 129.1 | 63 |
| Chemical formula 6 | >100 | >100 |
| Chemical formula 7 | >100 | >100 |
| Chemical formula 8 | 111.4 | 55 |
| Chemical formula 9 | >100 | >100 |
| Chemical formula 10 | 109.5 | 63 |
| Chemical formula 11 | >100 | >100 |
| Dihydrodictyopyrone derivatives | | |
| Chemical formula 3 | 56.2 | 15.9 |
| Chemical formula 4 | 42.5 | 19.7 |
| Chemical formula 12 | >50 | >50 |
| Chemical formula 13 | >50 | >50 |
| Chemical formula 14 | 54.1 | 29.5 |
| Chemical formula 15 | 88 | 43.4 |
| Chemical formula 16 | >100 | 31.1 |

The dictyopyrone derivatives represented by the chemical formulas 1, 2, and 8 and the dihydrodictyopyrone derivatives represented by the chemical formulas 3, 4, 15, and 16 had EC50 values equal to or less than ½ of their respective IC50 values. In particular, the compounds represented by the chemical formulas 1 to 4 (compounds 1 to 4) had EC50 values of less than 30 µM, that is, suppressed luciferase (OPN Luc) expression under control of OPN promoter by 50% at low concentration.

<B: Effect of Compound 3 on Suppressing OPN Production by Human Non-Small Cell Lung Cancer-Derived Cell Line A549 and Human Liver Cancer-Derived Cell Line HepG2>

As described above, some of the dictyopyrone derivatives and dihydrodictyopyrone derivatives were confirmed to inhibit luciferase expression under control of OPN promoter by 50% at a concentration equal to or less than ½ of their respective 50% cell growth inhibition concentrations (IC50). Therefore, the compound represented by the chemical formula 3 (compound 3) whose EC50 value is lowest and IC50 value is two times or more its EC50 value was subjected to a confirmation test to determine whether or not it could actually suppress OPN production by a cancer cell-derived cell line.

The confirmation test was performed in the following manner. The compound 3 wad added to a culture liquid containing cells of a human non-small cell lung cancer-derived cell line A549 or a human liver cancer-derived cell line HepG2, and the amount of OPN in culture supernatant after 2-day culture was measured using Human Osteopontin Immunoassay kit (R&D systems) and compared with the OPN amount of a compound 3-free group (control group).

The compound 3 has also cell growth inhibitory effect. Therefore, in order to properly evaluate the OPN production-suppressing effect of the compound 3, 1×CCLR used in luciferase assay was added to cells remaining in each well after removal of culture supernatant to prepare a cell lysate, and the amount of protein in the cell lysate was measured using BCA Protein Assay Kit (Thermo Scientific). The influence of addition of the compound 3 on the amount of OPN production was evaluated by comparison of the amount of OPN per milligram of protein.

B1) Sample Preparation Method

First, A549 cells or HepG2 cells were suspended in DMEM medium containing 10% FCS and 1% P/S at 4×10$^4$ cells/mL to obtain a cell suspension, and 500 µL of the cell suspension was dispensed into each well of a 24-well plate. In order to perform the test in triplicate, 3 wells were prepared for a control group and 3 wells were prepared for each test compound-treated group at each concentration. The 24-well plate was incubated in a $CO_2$ incubator (at 37° C. and 5% $CO_2$) for 24±4 hours.

The compound 3 as a test compound was dissolved in DMSO to prepare a 50 mmol/L solution, and the solution was stored at −80° C. The compound 3 solution was diluted with DMSO to prepare a 3.75 mmol/L solution, a 7.5 mmol/L solution, and a 15 mmol/L solution. The 7.5 mmol/L compound 3 solution or the 15 mmol/L compound 3 solution was added in an amount of 2 µL to each well in which A549 cells were cultured. Only DMSO was added to each control well in an amount of 2 µL.

The 3.75 mmol/L compound 3 solution or the 7.5 mmol/L compound 3 solution was added in an amount of 2 µL to each well in which HepG2 cells were cultured. Only DMSO was added to each control well in an amount of 2 µL.

The 24-well plate was rocked back and forth and side to side to mix the solution in each well, and was then incubated in a $CO_2$ incubator (at 37° C. and 5% $CO_2$) for 48±4 hours. Then, the total amount of culture supernatant was transferred into a 1.5 mL tube, and 500 µL of D-PBS(−) was added to each well in which cells are remained.

The 24-well plate was gently rocked, and D-PBS(−) was removed, and 1×CCLR prepared by 5-fold diluting 5×CCLR used in luciferase assay with water was dispensed into each well in an amount of 200 µL. Then, the 24-well plate was rocked on a rocking shaker for 15 minutes.

After rocking the 24-well plate for 15 minutes, the cell lysate in each well of the 24-well plate was transferred into a 1.5 mL tube and centrifuged in a high-speed refrigerated micro centrifuge at 4° C. and 15000 rpm for 1 minute to remove impurities such as cell debris. The thus obtained supernatant was used as a sample for protein assay.

On the other hand, the culture supernatant transferred into a 1.5 mL tube was centrifuged in a high-speed refrigerated micro centrifuge at 4° C. and 15000 rpm for 1 minute to remove impurities such as cell debris. The thus obtained supernatant was used as a sample for ELISA.

B2) Measurement of Amount of OPN Protein

The sample for ELISA was diluted in the following manner.

A549 cells (20-fold dilution): sample 5 µL+culture medium 95 µL

HepG2 cells (80-fold dilution): sample 2 µL+culture medium 158 µL

Water of 1 mL was added to a vial of OPN standard supplied in an ELISA kit, and the solution in the vial was gently mixed and allowed to stand at room temperature for 15 minutes to prepare 200 ng/mL OPN Standard. Then, as shown in Table 2, the OPN standard was serially diluted with a diluent RD5-24 supplied in the kit.

TABLE 2

| Vial | Volume of RD5-24 prepared (μL) | Type and amount of OPN standard solution added | OPN concentration (ng/mL) |
|---|---|---|---|
| — | — | — | 200 |
| A | 540 μL | 60 μL of 200 ng/mL OPN Standard | 20 |
| B | 300 μL | 300 μL of vial A | 10 |
| C | 300 μL | 300 μL of vial B | 5 |
| D | 300 μL | 300 μL of vial C | 2.5 |
| E | 300 μL | 300 μL of vial D | 1.25 |
| F | 300 μL | 300 μL of vial E | 0.625 |
| G | 300 μL | 300 μL of vial F | 0.312 |
| H | 300 μL | — | 0 = Blank |

The necessary number of OPN Microplates and RD1-6 supplied in the kit were prepared, and 100 μL of RD1-6 was dispensed into each well. The diluted OPN Standard (vial A to H) or the sample was further added in an amount of 50 μL to each well containing RD1-6. Then, the upper end of each well was covered with a seal, and the OPN microplates were allowed to stand at room temperature for 2 hours. In this period, Wash Buffer Concentrate supplied in the kit was diluted with water to prepare Wash Buffer.

After allowing the OPN microplates to stand for 2 hours, the liquid in each well was removed. The Wash Buffer of 250 μL was dispensed into each well and then removed to wash each well. This washing operation was performed 4 times.

OPN conjugate of 200 μL was dispensed into each well. Then, the upper end of each well was covered with a seal, and the OPN microplates were allowed to stand at room temperature for 2 hours. In this period, Color Reagent A and Color Reagent B supplied in the kit were mixed in equal amount to prepare Substrate Solution.

After allowing the OPN microplates to stand for 2 hours, the liquid in each well was removed. The Wash Buffer of 250 μL was dispensed into each well and then removed to wash each well. This washing operation was performed 4 times.

The Substrate Solution of 200 μL was dispensed into each well, and then the OPN microplates were allowed to stand at room temperature for 30 minutes while being shielded from light. Then, Stop Solution supplied in the kit was added to each well in an amount of 50 μL, and the liquid in each well was gently mixed with a vortex mixer until the color of the liquid in each well was entirely changed from blue to yellow. After the mixing, absorbance values (at 450 nm and 570 nm) were measured using a microplate reader (Bio-Rad; Benchmark or Thermo Scientific; Varioskan Flash). The subtraction of the value at OD 570 nm from the value at OD 450 nm was performed on all the measured data, and the thus determined values were used for calculation performed later.

A calibration curve was prepared from the absorbance values of the calibration curve samples. The amount of OPN protein was calculated using the formula of the calibration curve from the absorbance value of each sample.

B3) Measurement of Total Amount of Protein in Cells

The sample for protein assay of 10 μL and water of 90 μL were mixed to dilute the sample 10-fold. Calibration curve samples were prepared by diluting a BSA solution with water as shown in Table 3.

TABLE 3

| Vial | Water (μL) | Type and volume of BSA solution added | BSA concentration (μg/mL) |
|---|---|---|---|
| — | — | — | 2000 |
| A | 140 μL | 20 μL of 2000 ng/mL BSA | 250 |
| B | 80 μL | 80 μL of vial A | 125 |
| C | 90 μL | 60 μL of vial B | 50 |
| D | 80 μL | 80 μL of vial C | 25 |
| E | 80 μL | 20 μL of vial D | 5 |
| F | 80 μL | — | 0 |

BCA Reagent A and BCA Reagent B supplied in a protein assay kit were mixed (50:1) to prepare Working Reagent. The calibration curve sample (vial A to F) or the 10-fold diluted sample for protein assay was dispensed into each well of a 96-well plate in an amount of 25 μL. In order to perform the assay in duplicate, 2 wells were prepared for a control group, and 2 wells were prepared for each test compound-treated group at each concentration.

The Working Reagent of 200 μL was added to each well, and the solution in each well was mixed for 30 seconds with a vortex mixer. The 96-well plate was heated at 60° C. for 30 minutes and then allowed to stand at room temperature for 15 minutes. Then, absorbance values (550 nm) were measured using a microplate reader (Bio-Rad; Benchmark or Thermo Scientific; Varioskan Flash).

A calibration curve was prepared from the absorbance values of the calibration curve samples, and the total protein concentration of the diluted sample in each well was calculated using the formula of the calibration curve. Further, the total protein concentration was multiplied by the dilution factor (10) to calculate the total protein concentration of the sample.

(Expression of OPN (Protein) Amount)

The OPN amount (amount per milliliter of culture supernatant) was converted to the amount of OPN per total amount (0.5 mL) of the sample for ELISA. This converted value was divided by the amount of protein in the total amount (0.2 mL) of the sample for protein assay derived from the same well as the sample for measuring OPN amount for conversion to the amount of OPN per milligram of total protein in cells. Based on the amount of OPN per milligram of protein, the influence of addition of the compound 3 was evaluated.

(Statistical Processing)

The statistical processing of the OPN amounts was performed using Excel statistics, Statcel 3. The OPN amounts of the samples of the compound 3 (test compound)-treated groups were subjected to Dunnett test for comparison with those of the control group on an Excel file.

FIG. 1 is a graph showing the effect of addition of the compound 3 on suppressing OPN production by A549 cells. It was confirmed that when the concentration of the compound 3 was 30 μmol/L or 60 μmol/L, the compound 3 significantly suppressed OPN production by A549 cells at a significance level of less than 5% or 1%, respectively as compared to the control group.

Figure 2:
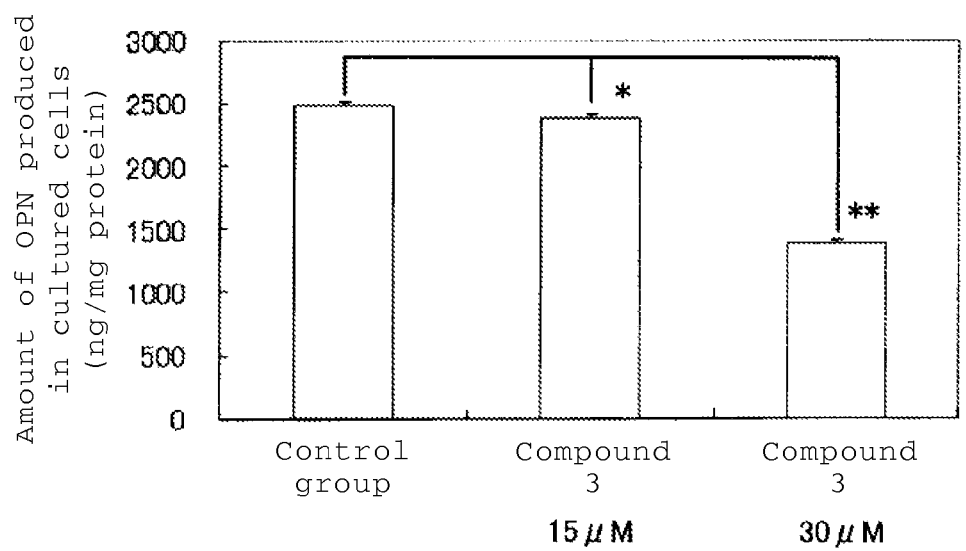
FIG. 2 is a graph showing the effect of addition of the compound 3 (compound represented by the chemical formula 3) on suppressing OPN production by HepG2 cells.

FIG. 2 is a graph showing the effect of addition of the compound 3 on suppressing OPN production by HepG2 cells. It was confirmed that when the concentration of the compound 3 was 15 μmol/L or 30 μmol/L, the compound 3 significantly suppressed OPN production by HepG2 cells at a significance level of less than 1% as compared to the control group. In particular, when the concentration of the compound 3 was 30 µmol/L, the amount of OPN produced by HepG2 cells was reduced to half or less of that of the control group.

It was confirmed from FIGS. 1 and 2 that the compound 3 significantly reduced the amount of OPN produced by a human non-small cell lung cancer-derived cell line A549 or by a human liver cancer-derived cell line HepG2.

<C: Effect of Compound 3 on Suppressing Wound-Healing Capacity of Human Non-Small Cell Lung Cancer-Derived Cell Line A549>

The experimental results shown in FIGS. 1 and 2 revealed that the compound 3 that suppresses luciferase expression under control of OPN promoter actually inhibited the production of OPN as protein. In the next stage, a determination was made as to whether or not the physiological function of cells induced by OPN production was suppressed by the compound 3 as a test compound. The determination was made by performing cell Wound-Healing assay. This assay is commonly known as a method for evaluating cell migration capacity. When a wound is made in a cell monolayer by scratching some cells with a pipette tip or the like, the wound is closed by migration of cells around the wound. The influence of a test compound on such function was observed by adding the test compound to a cell culture liquid.

C1) Method for Wound-Healing Assay

Cells of a human non-small cell lung cancer-derived cell line A549 were suspended in DMEM medium containing 10% FCS and 1% P/S at $3.5 \times 10^5$ cells/mL to obtain a cell suspension, and 500 µL ($1.75 \times 10^5$ cells) of the cell suspension was dispensed into each well of a 24-well plate. In order to perform the assay in triplicate, 3 wells were prepared for a control group and 3 wells were prepared for each test compound-treated group at each concentration. After the dispensing, the 24-well plate was incubated in a $CO_2$ incubator (at 37° C. and 5% $CO_2$) for 24±4 hours.

After the incubation, the medium was removed from all the wells, and a medium (serum-free medium) prepared by adding 0.1% bovine serum albumin (BSA) and 1% P/S to DMEM was dispensed into all the wells in an amount of 500 µL per well. The 24-well plate was rocked back and forth and side to side, and then the medium was again removed from all the wells. After removing the medium, the serum-free medium was dispensed into all the wells in an amount of 500 µL per well.

The compound 3 as a test compound was dissolved in DMSO to prepare a 50 mmol/L solution, and the solution was stored at −80° C. The compound 3 solution was diluted with DMSO to prepare a 3.125 mmol/L solution and a 6.25 mmol/L solution. The 3.125 mmol/L compound 3 solution or the 6.25 mmol/L compound 3 solution was added in an amount of 2 µL to each well in which A549 cells were cultured. Only DMSO was added to each control well in an amount of 2 µL.

The 24-well plate was rocked back and forth and side to side to mix the solution in each well, and was then incubated in a $CO_2$ incubator (at 37° C. and 5% $CO_2$) for 24±4 hours.

The cells in the 24-well plate were observed with a microscope to confirm that the cells were 100% confluent. Then, cells on the bottom surface of each well of the plate were scratched at three positions with a 20 µL-micropipette tip. As the microscope, IX71 inverted research microscope (OLYMPUS CORPORATION) equipped with Retiga-2000 Fast 1394 Color (QImaging) as a CCD camera system was used.

The wounds were observed with the microscope, and their images were taken in a single shot by adjusting the microscope. The magnification of the microscope was set to 40× (eyepiece: 10×, objective: 4×). After taking images, the 24-well plate was incubated in a $CO_2$ incubator (at 37° C. and 5% $CO_2$) for 48±4 hours.

After the incubation, the wounds were observed with the microscope, and their images were taken in a single shot by adjusting the microscope. The magnification of the microscope was set to 40× (eyepiece: 10×, objective: 4×).

Based on the taken images, the areas of the wounds were determined using Image-Pro Plus 7.0J (MediaCybernetics). Then, a wound healing rate (%) was calculated based on the following calculation formula: Wound healing rate (%)=100−[area of wound after 2 days from injury/area of wound just after injury]×100. The average wound-healing rates (%) of the control group and the two compound 3-treated groups at different concentrations were calculated. Further, the percentage of the wound-healing rate of the compound-treated group with respect to the wound-healing rate of the control group was also calculated.

C2) Statistical Processing

The statistical processing of calculated values of the wound-healing rate was performed using Excel statistics, Statcel 3. Specifically, all the wound-healing rates of the compound 3-treated groups were subjected to Dunnett test for comparison with the control group on an Excel file.

Figure 3:
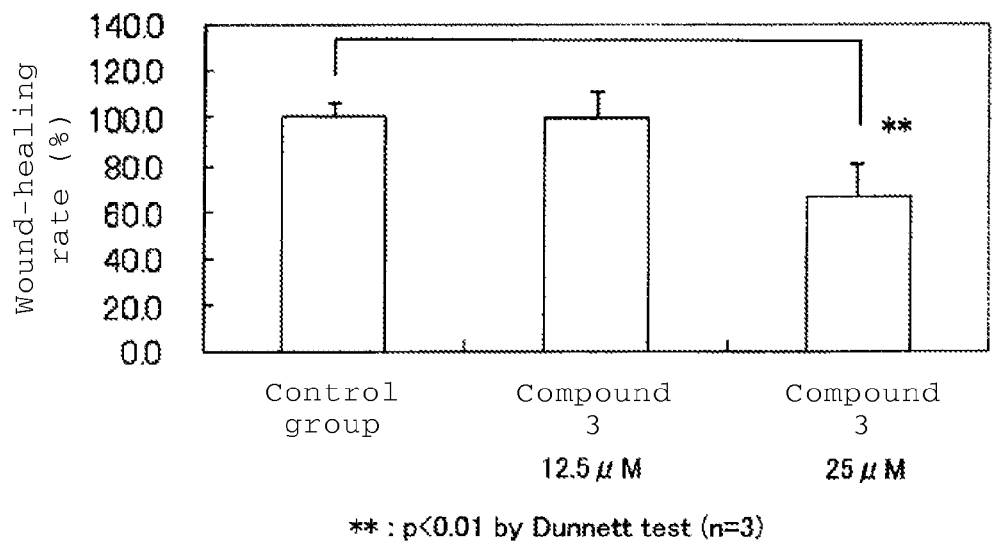
FIG. 3 is a graph showing the effect of addition of the compound 3 (compound represented by the chemical formula 3) on suppressing healing of wounds in A549 cells.

FIG. 3 is a graph showing the effect of addition of the compound 3 on suppressing wound healing in A549 cells. When the concentration of the compound 3 was 12.5 µmol/L, there was no difference in wound-healing rate between the compound 3-treated group and the control group, but when the concentration of the compound 3 was 25 µmol/L, there was a significant difference in wound-healing rate between the compound 3-treated group and the control group at a significance level of less than 1%. That is, it was confirmed that the compound 3 significantly suppressed wound healing in A549 cells at a concentration of 25 µmol/L.

<D: Effect of Compound 3 on Suppressing Metastatic and Invasive Capacity of Human Non-Small Cell Lung Cancer-Derived Cell Line A549>

As a second test for determining whether or not the physiological function of cells induced by OPN production is suppressed by a test compound, Matrix-Invasion assay was performed. In this assay, cups (inserts) whose bottom was covered with a membrane coated with collagen or laminin (Matrigel, BD Bioscience) as an extracellular matrix component and having ϕ8 µm pores and a 24-well plate for inserting the inserts were prepared. Cells suspended in a serum-free medium were placed in the inside insert, and a medium containing a substance inducing metastasis and invasion of cells (here, fetal calf serum) was injected into each well of the outside 24-well plate to determine the number of cells passing through the Matrigel-coated membrane of the insert and coming into the outside well.

Matrigel is an artificial basement membrane matrix for cell culture, more specifically a solubilized basement membrane preparation extracted from Engelbreth-Holm-Swarm (EHS) mouse sarcoma rich in extracellular matrix protein. Matrigel mainly contains laminin, collagen IV, heparan sulfate proteoglycan, and entactin/nidogen. Matrigel also contains TGF-β, epidermal growth factor, insulin-like growth factor, fibroblast growth factor, tissue plasminogen activator, and other growth factors naturally produced by EHS tumors.

Specifically, a fluorescent dye was introduced into A549 cells invading outside the membrane, and then the cells were separated from the membrane to measure their fluorescence intensity. At the same time, a fluorescent dye was introduced also into a known number of cells for preparing a calibration curve, and a calibration curve was prepared from their fluorescence intensity. Then, the number of invading cells of a test sample containing an unknown number of cells was determined from the fitted curve.

Cancer cells produce OPN by stimulation of fetal calf serum added to the outside medium. However, when OPN is present in the culture liquid, the cells produce Matrix Metalloproteinase (MMP) that is a collagen-degrading enzyme so that Matrigel is dissolved, and in addition, the cells transfer to the outside well due to their improved migration capacity. As a representative for the dictyopyrone derivatives and dihydrodictyopyrone derivatives that suppress luciferase expression under control of OPN promoter, the effect of the compound 3 on suppressing matrix-invasive function of A549 cells was observed.

D1) Method for Matrix-Invasion Assay

Cells of a human non-small cell lung cancer-derived cell line A549 were suspended in DMEM medium containing 10% FCS and 1% P/S at $1.8 \times 10^5$ cells/mL to obtain a cell suspension. The cell suspension of 10 mL was dispensed into a 75-cm$^2$ flask and incubated in a $CO_2$ incubator (at 37° C. and 5% $CO_2$) for 24±4 hours. In the same manner, a A549 cell suspension for preparing a calibration curve was prepared at $6 \times 10^4$ cells/mL. The cell suspension of 5 mL was dispensed into a 25-cm$^2$ flask and incubated in a $CO_2$ incubator (at 37° C. and 5% $CO_2$) for 24±4 hours. This day was counted as Day 0 of operation.

<Next Day: Day 1 of Operation>

The medium was removed from the 75-cm$^2$ flask into which the cells had been seeded. DMEM medium (serum-free medium) containing 0.1% BSA and 1% P/S of 10 mL was dispensed into the flask from which the medium had been removed, and the flask was rocked back and forth and side to side so that the entire cell surface was evenly covered with the medium. Then, the medium was removed from the flask.

Into the flask from which the medium had been removed, 10 mL of the serum-free medium was dispensed. Then, the flask was incubated in a $CO_2$ incubator (at 37° C. and 5% $CO_2$) for 24±4 hours.

<Day 2 of Operation>

Matrigel (10 mg/mL: BD Biosciences) was thawed on ice. Cell culture inserts (for 24-well plates, with 8.0 μm pores: BD Biosciences) and the serum-free medium were cooled in ice before use. The Matrigel was 25-fold diluted with the serum-free medium cooled in ice to prepare a Matrigel solution.

The necessary number of cell culture inserts were set in the 24-well plate, and the Matrigel solution was dispensed into the cell culture inserts in an amount of 50 μL per insert and spread over the entire membrane with a pipette chip tip. Then, the 24-well plate was incubated in a $CO_2$ incubator (at 37° C. and 5% $CO_2$) for 1 to 2 hours.

Cell culture supernatant was removed from the 75-cm$^2$ flask in which medium replacement with the serum-free medium was performed on the previous day. Calcium-magnesium-free phosphate buffered saline (D-PBS(−)) of 10 mL was dispensed into the flask, and the flask was rocked back and forth and side to side so that the entire cell surface was evenly covered with D-PBS(−), and then D-PBS(−) was removed (this operation is referred to as "washing with D-PBS(−)"). Then, 3 to 5 mL of Cell Dissociation Solution (CDS: Sigma) was dispensed into the flask. The flask containing CDS was incubated in a $CO_2$ incubator (at 37° C. and 5% $CO_2$) for about 20 minutes (with rocking every 5 minutes) to dissociate the cells from the bottom of the flask (this operation is referred to as "cell dissociation with CDS").

The flask was centrifuged at 300×g, and then the supernatant was removed and the cells were suspended in 5 mL of the serum-free medium to obtain a cell suspension. Part of the cell suspension (10 μL) was taken and mixed with 10 μL of a 0.4% trypan blue solution with gentle pipetting. Then, the number of cells was counted using Burker-Turk counting chamber to determine a cell concentration (this operation is referred to as "cell counting").

A cell suspension with a cell concentration of $2 \times 10^5$ cells/mL was prepared in an amount of 8 mL using the serum-free medium. The prepared cell suspension was gently dispensed into the culture inserts, incubated in a $CO_2$ incubator for 1 to 2 hours after coating their respective surfaces with the Matrigel solution, in an amount of 0.5 mL ($1 \times 10^5$ cells) per culture insert. The assay was performed in triplicate.

DMEM medium containing 10% FCS and 1% P/S was dispensed into 15-mL tubes in an amount of 5 mL per tube. The 50 mmol/L solution of the compound 3 in DMSO was dispensed into the tubes in an amount of 2.5 μL (final concentration: 25 μmol/L) or 5 μL (final concentration: 50 μmol/L) per tube to prepare a compound 3-supplemented medium. Doxycycline having the effect of suppressing metastasis and invasion (DOXY; a 100 mmol/L solution was previously prepared using DMSO and stored at −30° C.) was used as a positive control. The 100 mmol/L doxycycline solution of 3.75 μL (final concentration: 75 μmol/L) was added to 5 mL of DMEM medium containing 10% FBS and 1% P/S to prepare a positive control-supplemented medium. A negative control-supplemented medium was prepared by adding 5 μL of DMSO to 5 mL of DMEM medium containing 10% FCS and 1% P/S.

The compound 3-supplemented medium, the positive control-supplemented medium, or the negative control-supplemented medium was dispensed into each well of the 24-well plate in an amount of 0.75 mL through a gap between the culture insert and the plate. Then, the 24-well plate was incubated in a $CO_2$ incubator (at 37° C. and 5% $CO_2$) for 48±4 hours.

<Day 3 of Operation>

The medium in the 25-cm$^2$ flask in which A549 cells were cultured was removed and replaced with 5 mL of the serum-free medium. Then, the 25-cm$^2$ flask was incubated in a $CO_2$ incubator (at 37° C. and 5% $CO_2$) for 24±4 hours.

<Day 4 of Operation>

A calcein-AM vial (50 μg/vial: BD Biosciences) was returned to room temperature, and 30 μL of DMSO was added to and mixed with calcein-AM to prepare a calcein-AM solution. CDS of 5 mL was dispensed into a 15-mL tube, and 6 μL of the calcein-AM solution was added to and mixed with CDS to prepare a 1× calcein-AM solution (calcein-AM solution for inserts under test). On the other hand, CDS of 1.5 mL was dispensed into a 1.5-mL tube, and 3.6 μL of the calcein-AM solution was added to and mixed with CDS to prepare a 2× calcein-AM solution (calcein-AM solution for calibration curve).

D2) Preparation of Cells for Calibration Curve

Cell culture supernatant was removed from the 25-cm$^2$ flask in which medium replacement was performed on the previous day, and the above-described washing was performed using 5 mL of D-PBS(−). Further, the above-described cell dissociation was performed using 3 mL of CDS. Then, the above-described cell counting was performed, and a cell suspension was prepared at $5 \times 10^5$ cells/mL using CDS. Then, as shown in Table 4, the cell suspension was diluted with CDS. The cell suspension in each of vials A to H was dispensed into each well of a 96-well black plate (Corning) in an amount of 50 µL. The assay was performed in triplicate.

TABLE 4

| Vial | Cells/mL | Mixing ratio Suspension (mL) | CDS (mL) | Cells/well |
|---|---|---|---|---|
| A | $5 \times 10^5$ | Cell suspension | | 25000 |
| B | $2 \times 10^5$ | Vial A 0.4 | 0.6 | 10000 |
| C | $1 \times 10^5$ | Vial B 0.5 | 0.5 | 5000 |
| D | $5 \times 10^4$ | Vial C 0.5 | 0.5 | 2500 |
| E | $2 \times 10^4$ | Vial D 0.4 | 0.6 | 1000 |
| F | $1 \times 10^4$ | Vial E 0.5 | 0.5 | 500 |
| G | $5 \times 10^3$ | Vial F 0.5 | 0.5 | 250 |
| H | 0 | 0 | 0.5 | 0 |

D3) Calcein-AM Staining

D-PBS(−) of 0.75 mL was dispensed into each well of a fresh 24 well-plate. The medium in each insert was removed with a pipette while the insert was picked up with tweezers, and the insert was inserted into each well containing 0.75 mL of D-PBS(−). D-PBS(−) of 0.5 mL was dispensed into each insert to wash the insert with D-PBS(−).

A new 24-well plate was prepared, and the 1× calcein-AM solution of 0.35 mL was dispensed into each well of the 24-well plate. D-PBS(−) in each insert washed with D-PBS (−) was removed with a pipette while the insert was picked up with tweezers, and the insert was transferred into each well containing the 1× calcein-AM solution (fluorescence staining of cells in inserts under test). The 24-well plate with the transferred inserts was incubated in a $CO_2$ incubator (at 37° C. and 5% $CO_2$) for 1 hour while the side of the plate was gently tapped every 30 minutes.

During the incubation, the 2× calcein-AM solution of 50 µL was dispensed into each well of the 96-well black plate containing the cell suspension, and the 96-well black plate was wrapped with aluminum foil and allowed to stand at room temperature (staining of cells for calibration curve).

D4) Fluorescence Measurement

After the 1-hour incubation, the 24-well plate with inserts was rocked carefully so that the liquid in each well was mixed without spilling. Then, each insert was removed with tweezers from each well of the 24-well plate. The liquid in each well from which the insert had been removed was transferred into 3 wells of a fresh 96-well black plate in an amount of 100 µL per well (plate for cells in inserts under test).

The fluorescence of each well of each of the 96-well black plate for cells for calibration curve and the 96-well black plate for cells in inserts under test was measured (excitation: 485 nm, emission: 520 nm) using a microplate reader (Molecular Device; SpectraMax M5 or Thermo Scientific; Varioskan Flash).

D5) Calculation of Total Number of Invading Cells

The fluorescence intensity (RLU) values of the cells for calibration curve were input into Excel to determine the formula of a fitted curve (calibration curve) by the method of least squares. The number of invading cells was calculated using the formula of the calibration curve from the fluorescence intensity value of each well of the 96-well plate. The thus calculated number of invading cells was multiplied by 3.5 to determine the total number of invading cells per well of the 24-well plate. Further, since the assay was performed in triplicate, the average of total numbers of invading cells of 3 wells was calculated.

D6) Statistical Processing

Statistical processing was performed using Excel statistics, Statcel 3. The total numbers of invading cells of the positive control group and the compound 3-treated group were subjected to Dunnett test for comparison with those of the negative control group (control group) on an Excel file.

Figure 4:
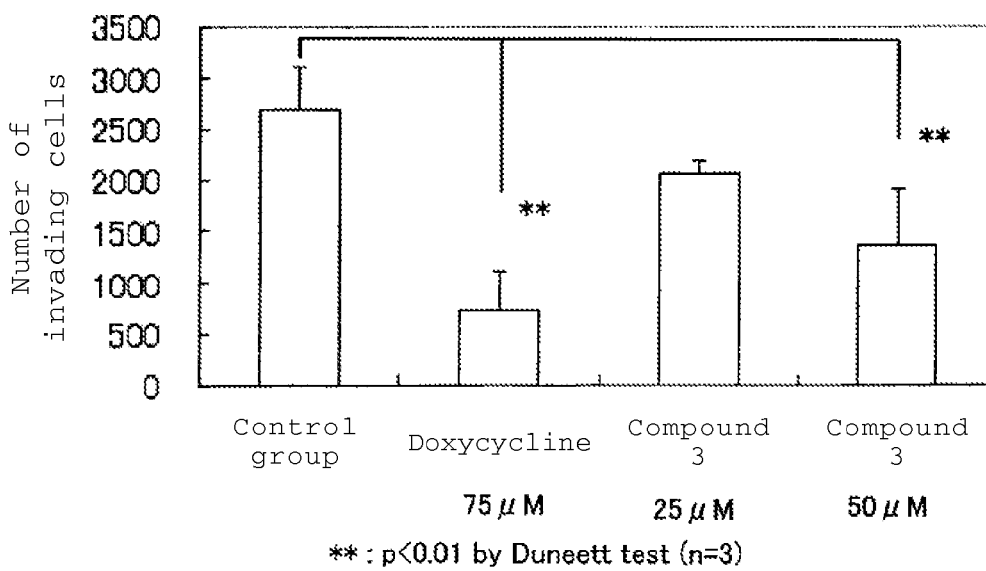
FIG. 4 is a graph showing the effect of addition of the compound 3 (compound represented by the chemical formula 3) on suppressing matrix invasion by A549 cells.

FIG. 4 is a graph showing the effect of addition of the compound 3 on suppressing matrix invasion by A549 cells. The total number of invading cells of the positive control group (doxycycline-treated group) was equal to or less than ⅓ of that of the control group. On the other hand, the total number of invading cells of the compound 3-treated group was smaller than that of the control group at a concentration of 25 µmol/L, but there was no significant difference between these groups. However, the total number of invading cells of the compound 3-treated group was about half of that of the control group at a concentration of 50 µmol/L, and there was a significant difference between these groups at a significance level of less than 1%. That is, it was confirmed that the compound 3 significantly suppressed matrix invasion by A549 cells at a concentration of 50 µmol/L.

<E. Influence of Mevalonic Acid on OPN Production Inhibitory Effect>

Statin-based drugs for treatment of hypercholesteremia (specifically, rosuvastatin, rovastatin, simvastatin, pravastatin, fluvastatin, atorvastatin, cerivastatin, pitavastatin, and mevastatin) are HMG-CoA reductase inhibitors. It is considered that such HMG-CoA reductase inhibitors have OPN production inhibitory effect because they inhibit HMG-CoA reductase and therefore reduce mevalonic acid so that a G-protein such as Ras is influenced by a reduction in the amount of isoprenoid derived from mevalonic acid (Non-patent Literature 8).

In order to determine whether the OPN production inhibitory effect of a dictyopyrone derivative or a dihydrodictyopyrone derivative contained as an active ingredient in the OPN production inhibitor according to the present invention is based on the same mechanism of action as a well-known statin-based drug for treatment of hypercholesteremia, simvastatin or the compound 3 was added to a culture liquid containing A549/OPNluc cells to determine its effect on gene expression under control of OPN promoter and to observe whether or not the effect was maintained even in the presence of mevalonic acid.

E1) WST Assay

A549/OPNluc cells were suspended in DMEM medium containing 10% FCS and 1% P/S at $3 \times 10^4$ cells/mL to obtain a cell suspension. The cell suspension of 100 µL was dispensed into each well of a 96-well plate, and the 96-well plate was incubated in a $CO_2$ incubator (at 37° C. and 5% $CO_2$) for 24±4 hours.

The 50 mmol/L solution of the compound 3 in DMSO stored at −80° C. was thawed by allowing it to stand at room temperature, and was then diluted with DMSO to prepare a 5.0 mmol/L solution. On the other hand, simvastatin (SVS: Sigma) was dissolved in DMSO to prepare a 50 mmol/L SVS solution, and the SVS solution was stored at −80° C. This SVS solution was thawed by allowing it to stand at room temperature before use and diluted with DMSO to prepare a 1 mmol/L SVS solution.

Mevalonic acid (MVA: Sigma) was dissolved in ethanol to prepare a 0.5 mol/L MVA solution, and the MVA solution was stored at −80° C. This MVA solution was thawed by allowing it to stand at room temperature before use, and was then allowed to stand at 37° C. for 30 minutes. Then, the MVA solution was diluted with D-PBS(−) to prepare a 20 mmol/L MVA solution and a 200 mmol/L MVA solution. The prepared MVA solutions were allowed to stand in a $CO_2$ incubator (at 37° C. and 5% $CO_2$) for 20 minutes (during incubation, these solutions were sometimes mixed).

The 20 mmol/L MVA solution or the 200 mmol/L MVA solution was added in an amount of 0.5 μL to each well containing the cell suspension (MVA 100 μmol/L:4 wells, MVA 1 mmol/L:4 wells). The solution in each well was mixed using a vortex mixer, and then the 96-well plate was incubated in a $CO_2$ incubator (at 37° C. and 5% $CO_2$) for 4 hours.

The 5.0 mmol/L solution of the compound 3 was added to the 4 wells containing MVA previously added at 100 μmol/L or 1 mmol/L in an amount of 0.5 μL per well. At the same time, the 5.0 mmol/L solution of the compound 3 was added also to 2 wells containing no MVA in an amount of 0.5 μL per well. Further, the 1 mmol/L SVS solution was added to the 4 wells containing MVA at 100 μmol/L or 1 mmol/L in an amount of 0.5 μL per well. At the same time, the 1 mmol/L SVS solution was added also to 2 wells containing no MVA in an amount of 0.5 μL per well. DMSO was added to 2 wells containing none of MVA as a control drug, the compound 3, and SVS in an amount of 0.5 μL per well (Control). Table 5 shows the type and amount of drug added to each test group.

TABLE 5

| Test group | Type and amount of drug added | Number of wells |
|---|---|---|
| Control | DMSO 0.5 μL | 2 |
| Compound 3: 25 μM | Compound 3: 5.0 mmol/L 0.5 μL | 2 |
| Compound 3: 25 μM + MVA: 100 μM | Compound 3: 5.0 mmol/L 0.5 μL + MVA: 20 mmol/L 0.5 μL | 2 |
| Compound 3: 25 μM + MVA: 1 mM | Compound 3: 5.0 mmol/L 0.5 μL + MVA: 200 mmol/L 0.5 μL | 2 |
| SVS: 5 μM | SVS: 1 mmol/L 0.5 μL | 2 |
| SVS: 5 μM + MVA: 100 μM | SVS: 1 mmol/L + MVA: 20 mmol/L 0.5 μL | 2 |
| SVS: 5 μM + MVA: 1 μM | SVS: 1 mmol/L + MVA: 200 mmol/L 0.5 μL | 2 |

The solution in each well was mixed with a vortex mixer, and then the 96-well plate was incubated in a $CO_2$ incubator (at 37° C. and 5% $CO_2$) for 48±4 hours. Then, Premix WST-1 Reagent (TAKARA BIO INC.) of 10 μL was added to each well. The solution in each well was mixed with a vortex mixer, and then the 96-well plate was incubated at 37° C. and 5% $CO_2$. After 30 min, 90 min, and 120 min, absorbance values (450 nm) were measured using a microplate reader (Bio-Rad; Benchmark or Thermo Scientific; Varioskan Flash).

The absorbance values were input into an Excel file, and the absorbance values of all the samples of each test group were divided by the average absorbance value of Control to determine the ratio of the absorbance value of each sample to the absorbance value of Control (Ratio to Control).

Absorbance value of each sample÷absorbance value of Control=Ratio to Control

E2) Luciferase Assay

After the WST assay, the supernatant in each well was removed, and D-PBS(−) of 100 μL was dispensed into each well. Luciferase Assay Substrate (LAS) supplied in Luciferase Assay Systems (Promega) was dissolved in Luciferase Assay Buffer (LAB) to prepare a luciferase reagent. Further, 5×CCLR was 5-fold diluted with water to prepare 1×CCLR.

D-PBS(−) in each well was completely removed, and 1×CCLR of 50 μL was dispensed into each well. Then, the 96-well plate was allowed to stand at room temperature for 30 minutes. After allowing the 96-well plate to stand, 1×CCLR in each well was used as a measurement sample. The luciferase reagent of 100 μL was dispensed into a tube for chemiluminescence measurement, and 20 μL of the measurement sample was added to the tube and mixed with the luciferase reagent. The chemiluminescence (Relative Light Unit: RLU) of the measurement sample was measured using GloMax 20/20 Luminometer (Promega).

The RLU values of Control and the RLU values of each measurement sample were input into an Excel file. The RLU value of each measurement sample was divided by the value of Ratio to Control determined by WST assay to correct a difference in RLU value caused by a difference in cell growth rate influenced by addition of the compound 3 or SVS.

Figure 5:
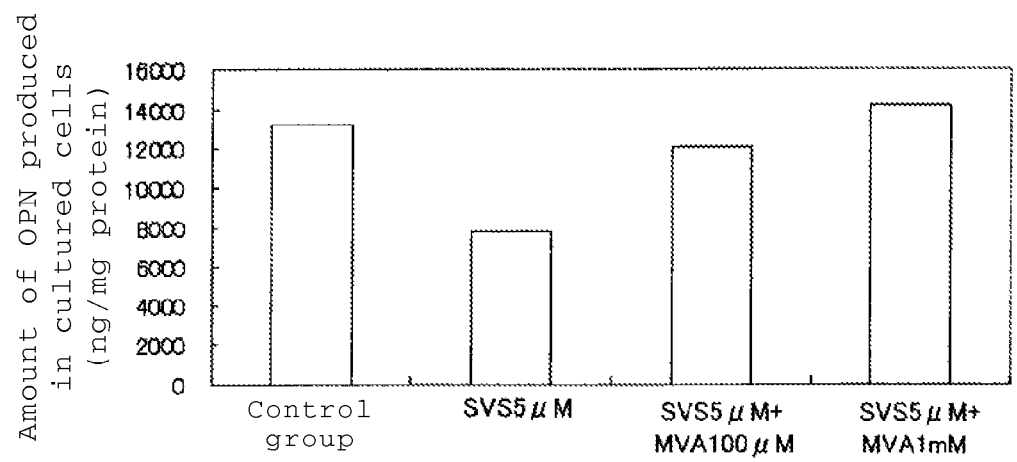
FIG. 5 is a graph showing the effect of addition of MVA (mevalonic acid) on recovering OPN production suppressed by SVS (simvastatin).

FIG. 5 is a graph showing the effect of addition of MVA on recovering luciferase activity suppressed by SVS. The addition of SVS reduced luciferase activity of A549 cells under control of OPN promoter. However, it was confirmed that addition of MVA at 100 μmol/L or 1 mmol/L erased the luciferase activity-suppressing effect of SVS so that the luciferase activity of A549 cells was recovered to the same level as Control.

Figure 6:
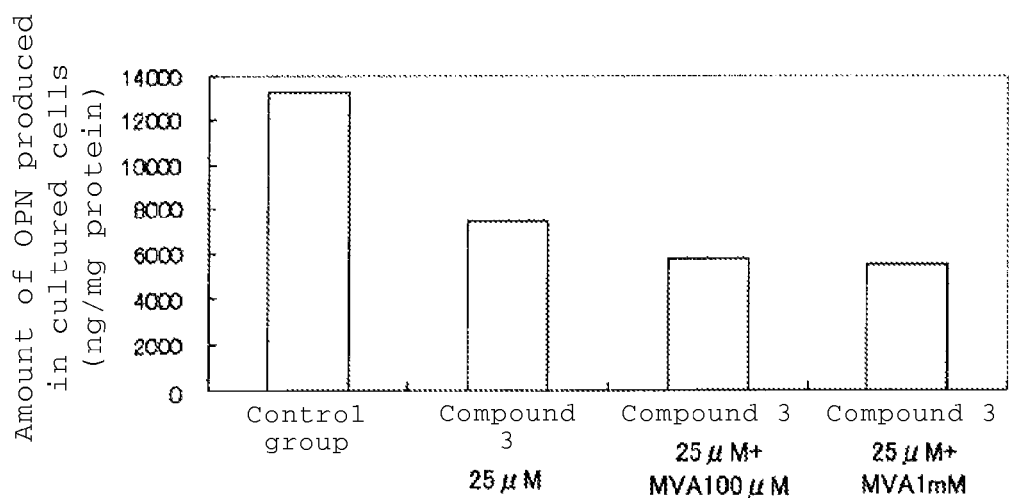
FIG. 6 is a graph showing the influence of MVA addition on the OPN production-suppressing effect of the compound 3.

FIG. 6 is a graph showing the effect of addition of MVA on the luciferase activity-suppressing effect of the compound 3. As shown in FIG. 6, suppression of luciferase activity caused by addition of the compound 3 was not recovered by addition of MVA.

The results shown in FIGS. 5 and 6 suggested that SVS and the compound 3 had different mechanisms of action in suppressing luciferase activity.

INDUSTRIAL APPLICABILITY

The OPN production inhibitor according to the present invention containing a dictyopyrone derivative or a dihydrodictyopyrone derivative as an active ingredient is expected to prevent a disease, such as cancer metastatis, resulting from increased OPN production. The OPN production inhibitor according to the present invention containing a dictyopyrone derivative or a dihydrodictyopyrone derivative as an active ingredient is useful in the fields of pharmaceuticals, biochemistry, and biotechnology as an OPN production inhibitor whose mechanism of action is different from that of a conventional OPN production inhibitor.

The invention claimed is:

1. An osteopontin production inhibitor comprising a compound dictyopyrone derivative represented by the following chemical formula 1 as an active ingredient:

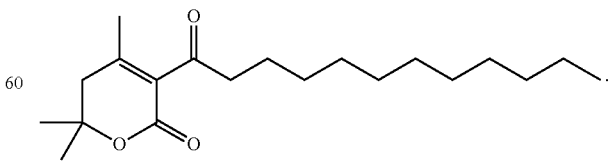

Chemical Formula 1

2. An osteopontin production inhibitor comprising a compound dictyopyrone derivative represented by the following chemical formula 4 as an active ingredient:

Chemical Formula 4

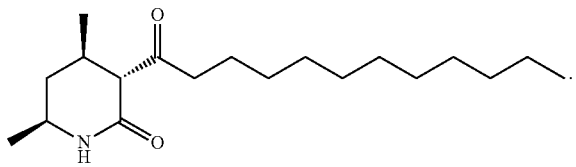

3. An osteopontin production inhibitor comprising a compound dictyopyrone derivative represented by the following chemical formula 10 as an active ingredient:

Chemical Formula 10

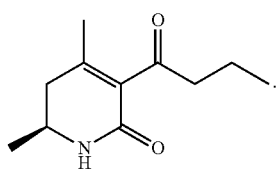

4. An osteopontin production inhibitor comprising a compound dictyopyrone derivative represented by the following chemical formula 14 or 16 as an active ingredient:

Chemical Formula 14

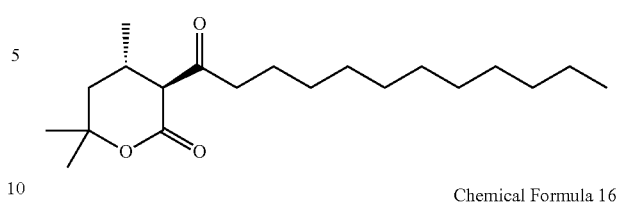

5. The osteopontin production inhibitor of claim 4, wherein the compound is represented by the chemical formula 14.

6. The osteopontin production inhibitor of claim 4, wherein the compound is represented by the chemical formula 16.

* * * * *